(12) United States Patent
Watson et al.

(10) Patent No.: US 12,296,285 B2
(45) Date of Patent: May 13, 2025

(54) METHODS FOR PURIFYING ANTIBODIES

(71) Applicant: UCB BIOPHARMA SRL, Brussels (BE)

(72) Inventors: Neil Alan Watson, Slough Berkshire (GB); Curtis William Phippen, Slough Berkshire (GB)

(73) Assignee: UCB BIOPHARMA SRL, Brussels (BE)

( * ) Notice: Subject to any disclaimer, the term of this patent is extended or adjusted under 35 U.S.C. 154(b) by 633 days.

(21) Appl. No.: 17/631,897

(22) PCT Filed: Jul. 30, 2020

(86) PCT No.: PCT/EP2020/071533
§ 371 (c)(1),
(2) Date: Feb. 1, 2022

(87) PCT Pub. No.: WO2021/023619
PCT Pub. Date: Feb. 11, 2021

(65) Prior Publication Data
US 2022/0280887 A1   Sep. 8, 2022

(30) Foreign Application Priority Data
Aug. 2, 2019   (EP) .................................. 19189841

(51) Int. Cl.
| C07K 1/18 | (2006.01) |
| B01D 15/38 | (2006.01) |
| C07K 1/22 | (2006.01) |
| C07K 16/06 | (2006.01) |
| C07K 16/12 | (2006.01) |

(52) U.S. Cl.
CPC ............ *B01D 15/3809* (2013.01); *C07K 1/18* (2013.01); *C07K 1/22* (2013.01); *C07K 16/065* (2013.01); *C07K 16/12* (2013.01)

(58) Field of Classification Search
None
See application file for complete search history.

(56) References Cited

U.S. PATENT DOCUMENTS

| 5,726,293 A | 3/1998 | Seed |
| 2004/0063153 A1 | 4/2004 | Jelinek et al. |
| 2013/0096284 A1 | 4/2013 | Ishihara |
| 2018/0100007 A1* | 4/2018 | Heywood .............. C07K 16/18 |

FOREIGN PATENT DOCUMENTS

| JP | 2015020955 | 2/2015 |
| WO | WO 2011/162210 | 12/2011 |

OTHER PUBLICATIONS

Imidazole Elution Buffer. Cold Spring Harbor Protocols. doi:10.1101/pdb.rec356 Cold Spring Harb Protoc, 2006.*
Purifying Challenging Proteins Principles and Methods GE Healthcare. Handbook 28-9095-31 AA, 2007.*
Ishihara, T. et al. "Improving impurities clearance by amino acids addition to buffer solutions for chromatographic purifications of monoclonal antibodies" *Journal of Chromatography B*, available online May 18, 2015, pp. 107-114, vols. 995-996.
Aruffo, A. et al. "CD62/P-Selectin Recognition of Myeloid and Tumor Cell Sulfatides" *Cell*, Oct. 4, 1991, pp. 35-44, vol. 67, No. 1.
Written Opinion in International Application No. PCT/EP2020/071533, Nov. 25, 2020, pp. 1-5.

* cited by examiner

*Primary Examiner* — Oluwatosin A Ogunbiyi
(74) *Attorney, Agent, or Firm* — SALIWANCHIK, LLOYD & EISENSCHENK

(57) ABSTRACT

The invention relates to the field of manufacturing recombinant antibody molecules. In particular, methods of purifying such recombinant antibody molecules are provided wherein imidazole or an imidazole-analogue is added during the elution of the recombinant antibody molecule from an affinity chromatography resin, such as a protein-A-based resin.

7 Claims, 7 Drawing Sheets
Specification includes a Sequence Listing.

METHODS FOR PURIFYING ANTIBODIES

CROSS-REFERENCE TO RELATED APPLICATION

This application is the U.S. national stage application of International Patent Application No. PCT/EP2020/071533, filed Jul. 30, 2020.

REFERENCE TO SEQUENCE LISTING

The Sequence Listing for this application is labeled "Seq-List.txt" which was created on Nov. 8, 2021 and is 10 KB. The entire content of the sequence listing is incorporated herein by reference in its entirety.

FIELD OF THE INVENTION

The current invention relates to the field of manufacturing recombinant antibody molecules and in particular to a method of purifying such recombinant antibody molecules using affinity chromatography and the use of particular elution conditions.

BACKGROUND OF THE INVENTION

In the field of therapeutics, the use of biological entities such as proteins, including antibodies and antibody-derived molecules in particular, has been constantly gaining presence and importance, and, with it, the need for controlled large-scale manufacturing processes has developed in parallel.

Protein A is a cell wall component produced by several strains of Staphylococcus aureus that binds to the Fc region of antibody molecules. Affinity chromatography using immobilized protein A as a ligand has been extensively used for antibody purification and remains to date the core purification step in most antibody purification processes, allowing a high elimination of impurities from the starting material. Furthermore, protein A is also known to bind VH3 regions present on antibody molecules, giving rise to certain purification strategies for alternative antibody formats that lack an Fc region based on an affinity interaction between the VH3 region and protein A.

Protein A has high affinity for Fc domains at neutral pH. As a consequence, starting material containing the antibody to be purified is typically loaded on the protein A resin at neutral pH. A typical process will be followed by one or more steps of washing the chromatography material with a buffer that is also at neutral pH to ensure removal of as many impurities as possible. Finally, an elution step is necessary to recover the bound antibody from the protein A. This elution step involves the use of an elution buffer with an acidic pH (typically from about 2.5 to about 4.0) that will disrupt the interaction between the antibody and protein A. Similarly, WO2016/169992 describes purification methods for antibody molecules lacking an Fc region based on the binding of VH3 regions via protein A that also rely on acidification of the pH for elution from protein A.

Typically, a lower pH also allows a lower elution volume, which directly impacts the overall process efficiency. Another consideration regarding lower elution volumes is that they can enable the use of static binding conditions as opposed to the traditional dynamic binding conditions where a high volume of elution buffer is washed over the chromatography resin.

However, a balance must be found between the pH being low enough to disrupt the binding of the antibody molecule to protein A, but also not being so low as to disrupt the tertiary structure of the protein. Furthermore, aggregation is a frequent consequence of exposure to acidic conditions resulting in further impurities that must be removed during the purification process and ultimately in a lower process yield. As a consequence, for some antibody molecules that are more unstable, it can be advantageous to find conditions that allow for elution from protein A at a higher pH.

In an attempt to overcome these challenges, there have been different attempts to enhance elution of antibody molecules from protein A by adding additional components into the elution buffer that could compete with the antibody molecule for binding to protein A and/or increasing the elution pH.

Arakawa et al (Elution of antibodies from a Protein-A column by aqueous arginine solutions; 2004; Protein Expression & Purification, 244-248) and U.S. Pat. No. 8,470,328 describe the use of arginine or an arginine derivative in an elution buffer that has a pH of 4.0 to 5.0. However, as the pH of the elution buffer is increased so does the elution volume, as the high pH will only cause weak dissociation of the antibody from the resin, which can then also easily rebind to the resin.

A further consideration for commercial large-scale manufacturing process is the time each chromatography cycle takes, which in turn is directly impacted by the volumes that are used in the load, wash and elution of the chromatographic supports such as protein A. Optimization of these parameters in a small scale can have a large impact when scaled up to manufacturing volumes, resulting in improvements in terms of waste materials that must be disposed of, shorter production times, and consequently improved cost profiles.

Alternative forms of protein purification have also been used that involve expressing the recombinant protein with a histidine-tag, and then purifying the resulting protein using nickel affinity chromatography (that binds the histidine tags) and eluting the protein with the aid of imidazole. However, a disadvantage of this method is that for many uses, the tag will need to be removed proteolytically after purification before the protein can be used.

Based on the above there is a continuing need to provide rapid and robust methods for purifying antibodies during the manufacturing processes, and in particular for improved methods of eluting antibody from affinity chromatography resins. This need is addressed by the current invention.

SUMMARY OF THE INVENTION

In a first aspect, the invention relates to a method for purifying an antibody comprising:
  a) Loading a mixture comprising the antibody to be purified onto an affinity chromatography resin, wherein the affinity chromatography resin is not a nickel-based, zinc-based or cobalt-based resin,
  b) Washing the chromatographic resin with a wash buffer;
  c) Eluting the antibody with an elution buffer that comprises 0.01M to 1.0M imidazole or an imidazole-analogue and a pH of 3 to 5.

DETAILED DESCRIPTION OF THE INVENTION

Figure 1:
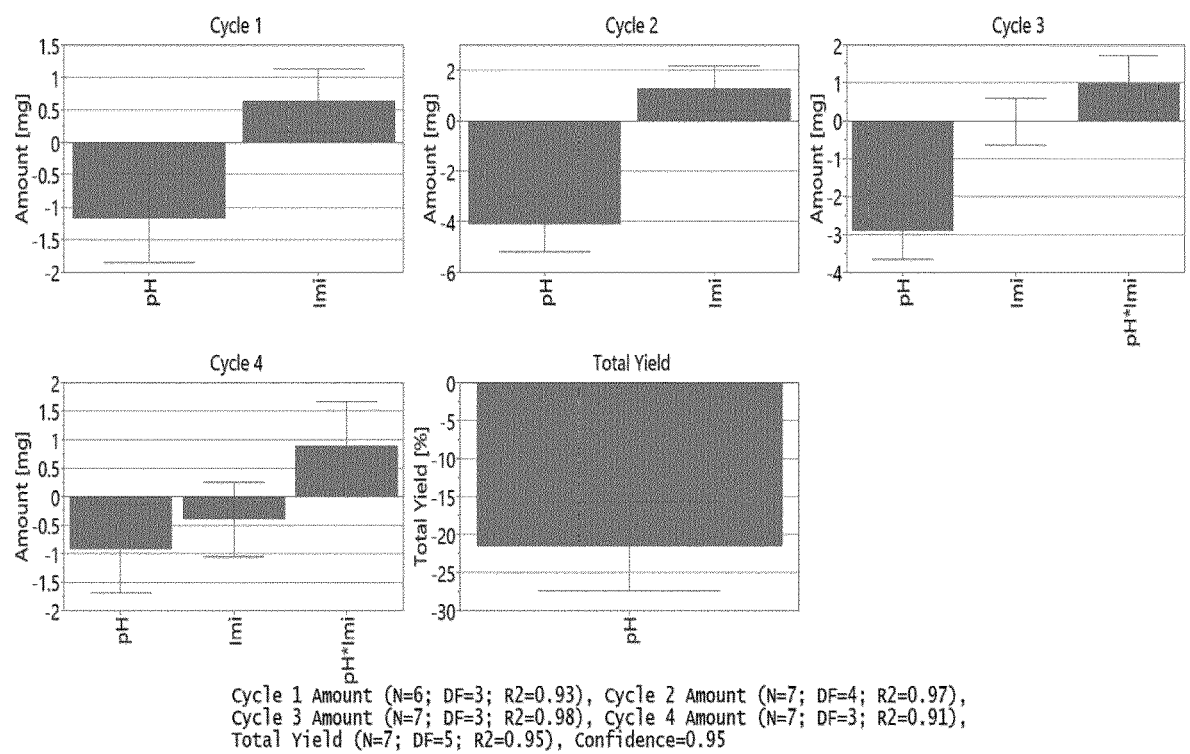
FIG. 1: Static Binding Study Results

The current invention solves the above-outlined problem by providing a novel method for purifying an antibody comprising an affinity chromatography step wherein the elution is performed in the presence of imidazole or an imidazole-analogue. Without being bound by any theory, it is believed that imidazole or analogues thereof bind antibody molecules that dissociate from the chromatographic resin during the elution step. Thereby, the imidazole, or analogue thereof, prevents rebinding of antibody molecules to the resin. This helps improve the elution kinetics, thus reducing the elution volume, which is an advantage over methods described in the art.

The method of the invention is suitable for antibody purification methods comprising an affinity chromatography step performed under both static and dynamic conditions.

In the context of the present invention dynamic conditions are considered those where the affinity resin is typically in a chromatography column or membrane and the mixture comprising the antibody to be purified, wash buffers and/or elution buffers are added over the column, and an eluate is recovered from the column. Static chromatographic conditions are those that involve mixing the chromatographic resin and the mixture comprising the antibody to be purified, followed by an incubation period, and subsequent separation of the chromatographic resin from the liquid phase and later elution of the bound fraction from the chromatographic resin.

In a preferred embodiment of the method of the invention, one, two or all of, of steps a), b) and c) are performed under dynamic conditions.

In a first aspect, the invention relates to a method for purifying an antibody comprising:
a) Loading a mixture comprising the antibody to be purified onto an affinity chromatography resin,
  wherein the affinity chromatography resin is not a nickel-based, zinc-based or cobalt-based resin,
b) Washing the chromatographic resin with a wash buffer, and
c) Eluting the antibody with an elution buffer that comprises 0.01M to 1.0M imidazole or an imidazole-analogue and a pH of 3 to 5.

The affinity chromatography resin is capable of binding the antibody, preferably through an Fc region or VH3 domain of the antibody. In one embodiment, said affinity chromatography resin is not a metal-ion-based resin. In another embodiment, said affinity chromatography resin is selected from: a protein A chromatography resin, a protein G chromatography resin and a protein L chromatography resin.

There are many affinity chromatography materials containing protein A, protein G or protein L available to the skilled artisan, such as for example MabSelect® (GE Healthcare), Absolute® (Novasep), Captiv A® (Repligen), Praesto AP (Purolite) or Amsphere® (JSR).

Buffers suitable for use as wash and elution buffers in protein A chromatography are readily available in the art, and may be chosen by way of non-limiting examples from among phosphate buffered saline (PBS), Tris, histidine, acetate, formate, citrate buffers, or MES (2-(N-morpholino) ethanesul phonic acid Imidazole), BES (N,N-(bis-2-hydroxyethyl)-2-aminoethanesulphonic acid), MOPS (3-(N-morpholino)-propanesulphonic acid), or HEPES (N-2-hydroxyethylpiperazine-N'-2-ethanesulphonic acid) buffers.

In one embodiment, the elution buffer comprises 0.01M to 0.75M imidazole or imidazole-analogue, such as 0.01M to 0.5M, e.g. 0.1M to 0.5M, such as 0.2M to 0.5M, e.g. 0.2M to 0.3M, such as 0.25M imidazole or imidazole-analogue.

In one embodiment, the pH of the elution buffer is 3.5-4.5, such as 3.5 to 4.0 or 4.0 to 4.5, or 3.6 to 3.9, e.g. 3.7 to 3.9.

In one embodiment, the wash buffer also comprises imidazole or an imidazole-analogue. In one embodiment, the wash buffer comprises 0.01M to 0.75M imidazole or imidazole-analogue, such as 0.01M to 0.5M, e.g. 0.1M to 0.5M, such as 0.2M to 0.5M, e.g. 0.2M to 0.3M, such as 0.25M imidazole or imidazole-analogue.

Imidazole is an organic compound with the formula $C_3N_2H_4$. It is an aromatic heterocycle, classified as a diazole, and has non-adjacent nitrogen atoms.

The term "imidazole-analogue" as used herein refers to imidazole or other 5-membered ring structures containing at least two nitrogen atoms (i.e. diazoles or triazoles), such as pyrazole and triazole.

The ring may be substituted or unsubstituted. If substitutions are present, they are, in one embodiment, selected from methyl, ethyl, hydroxyl or hydroxymethyl. In one embodiment, there is only one substitution, such as one methyl group. In another embodiment there are two substitutions, such as two methyl groups.

In one embodiment, the ring is not substituted at positions 1 or 2, such as an imidazole ring which is not substituted at positions 1 or 2 (Formula I).

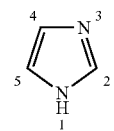

(Formula I - Imidazole)

Preferred imidazole-analogues include 4(5)-methylimidazole, pyrazole, 1,5-dimethyl-1H-pyrazole, 1,3-dimethyl-1H-pyrazole and 1H-Imidazole-1-ylmethanol.

In another embodiment, the imidazole-analog is histidine or a histidine-analog, such as n-boc-L-histidine, n-benzyloxycarbonyl-D-histidine or L-histidine methyl ester dihydrogen chloride.

In a preferred embodiment, the ring is unsubstituted, preferably unsubstituted imidazole or pyrazole.

In one embodiment, the method of the invention comprises a further step of equilibrating the chromatographic resin with an equilibration buffer comprising imidazole or an imidazole-analogue prior to loading of the mixture comprising the antibody onto the chromatographic resin.

In a further embodiment the method of the invention will comprise one or more additional chromatography steps to remove remaining impurities. Generally, such steps will employ a non-affinity chromatography step using a solid phase with appropriate functionality for use in gel filtration chromatography, cation chromatography, anion chromatography, mixed-mode chromatography, hydrophobic chromatography and hydrophobic charge induction chromatography. These may be operated in bind and elute mode or in flow-through mode. In flow-through mode, the impurities bind or have reduced mobility in the solid phase whereas the target protein is recovered in the eluate or flow-through fraction. Appropriate solid phases for use in chromatography such as beaded resins or membranes with the appropriate functionality are readily available to the skilled artisan. In a particular embodiment according to the method of the invention, the method additionally comprises a step of anion exchange chromatography operated in the flow-through mode.

In a further particular embodiment, the method of the invention comprises a protein A chromatography step followed by a first chromatography step that is an anion exchange chromatography producing a flow-through containing the protein and a second chromatography step that is a cation exchange chromatography from where an eluate containing the protein is recovered.

In another embodiment, the method of the invention comprises a protein A chromatography followed by a first chromatography step that is a cation exchange chromatography from where an eluate containing the protein is recovered, and a second chromatography step that is an anion exchange chromatography to produce a flow-through containing the protein.

Antibodies

The terms "antibody" or "antibodies" as used herein include monoclonal and polyclonal antibodies. Furthermore, the terms "antibody" or "antibodies" as used herein include, but are not limited to, recombinant antibodies that are generated by recombinant technologies as known in the art. "Antibody" or "antibodies" include antibodies' of any species, in particular of mammalian species; such as human antibodies of any isotype, including IgD, $IgG_1$, $IgG_{2a}$, $IgG_{2b}$, $IgG_3$, $IgG_4$ IgE and antibodies that are produced as dimers of this basic structure including $IgA_1$, $IgA_2$, or pentamers such as IgM and modified variants thereof, non-human primate antibodies, e.g. from chimpanzee, baboon, rhesus or cynomolgus monkey; rodent antibodies, e.g. from mouse, or rat; rabbit, goat or horse antibodies; and camelid antibodies (e.g. from camels or llamas such as Nanobodies™) and derivatives thereof; or of bird species such as chicken antibodies or of fish species such as shark antibodies. The term "antibody" or "antibodies" also refers to "chimeric" antibodies in which a first portion of at least one heavy and/or light chain antibody sequence is from a first species and a second portion of the heavy and/or light chain antibody sequence is from a second species. Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences. "Humanized" antibodies are chimeric antibodies that contain a sequence derived from non-human antibodies. For the most part, humanized antibodies are human antibodies (recipient antibody) in which residues from a hypervariable region of the recipient are replaced by residues from a hypervariable region [or complementarity determining region (CDR)] of a non-human species (donor antibody) such as mouse, rat, rabbit, chicken or non-human primate, having the desired specificity, affinity, and activity. In most instances residues of the human (recipient) antibody outside of the CDR; i.e. in the framework region (FR), are additionally replaced by corresponding non-human residues. Furthermore, humanized antibodies may comprise residues that are not found in the recipient antibody or in the donor antibody. These modifications are made to further refine antibody properties. Humanization reduces the immunogenicity of non-human antibodies in humans, thus facilitating the application of antibodies to the treatment of human disease. Humanized antibodies and several different technologies to generate them are well known in the art. The terms "antibody" or "antibodies" also refer to human antibodies, which can be generated as an alternative to humanization. For example, it is possible to produce transgenic animals (e.g., mice) that are capable, upon immunization, of producing a full repertoire of human antibodies in the absence of production of endogenous murine antibodies. Other methods for obtaining human antibodies/antibody fragments in vitro are based on display technologies such as phage display or ribosome display technology, wherein recombinant DNA libraries are used that are either generated at least in part artificially or from immunoglobulin variable (V) domain gene repertoires of donors. Phage and ribosome display technologies for generating human antibodies are well known in the art. Human antibodies may also be generated from isolated human B cells that are ex vivo immunized with an antigen of interest and subsequently fused to generate hybridomas which can then be screened for the optimal human antibody. The term "antibody" or "antibodies" as used herein, also refers to an aglycosylated antibody.

The term "antibody" or "antibodies" as used herein not only refers to full-length antibodies of any species, including from human (e.g. IgG) and other mammalian species, but also refers to an antibody fragment. A fragment of an antibody comprises at least one heavy or light chain immunoglobulin domain as known in the art and binds to one or more antigen(s). Examples of antibody fragments according to the invention include Fab, Fab', F(ab')2, and Fv and scFv fragments; as well as diabodies, triabodies, tetrabodies, minibodies, domain antibodies (dAbs), such as sdAbs, $V_HH$ and $V_{NAR}$ fragments, single-chain antibodies, bispecific, trispecific, tetraspecific or multispecific antibodies formed from antibody fragments or antibodies, including, but not limited to, Fab-Fv or Fab-Fv-Fv constructs. Antibody fragments as defined above are known in the art.

In one embodiment, the antibody that is purified using the method of the invention does not comprise any of the following motifs: a polyhistidine motif, an HQ motif, an HN motif or a HAT motif, wherein a polyhistidine motif is a sequence of five or more consecutive histidine residues, a HQ motif is a sequence comprising at least three alternations of histidine and glutamine (HQHQHQ (SEQ ID NO:7)), a HN motif is a sequence comprising at least three alternations of histidine and asparagine (HNHNHN (SEQ ID NO:8)) and a HAT motif is the sequence KDHLIHNVHKEEHA-HAHNK (SEQ ID NO:9).

In one embodiment of the method of the invention, the antibody to be purified is an antibody comprising an Fc region.

In one embodiment, the antibody to be purified is an antibody comprising a CH2 and a CH3 domain.

In one embodiment, the antibody to be purified is an antibody that contains a VH3 region and binds the affinity chromatography resin via the VH3 region.

In another embodiment, the antibody is selected from: IgG, Fab', F(ab')2, scFv, Fab-Fv, Fab-scFv, Fab-(scFv)2, Fab-(Fv)2, diabodies, triabodies, and tetrabodies.

In one embodiment of the method of the invention the antibody is a FabFv or disulfide stabilized form thereof as disclosed in PCT/EP2014/074409, incorporated herein by reference.

In one embodiment, the antibody comprises a binding domain specific to human serum albumin, in particular with CDRs or variable regions as disclosed in WO2013/068563, incorporated herein by reference.

In one embodiment the antibody, such as a Fab-dsFv format is one disclosed in PCT/EP2014/074409 or WO2014/019727, incorporated herein by reference.

In another embodiment the antibody is a Fab-scFv fusion protein format disclosed in WO2013/068571, incorporated herein by reference.

In another embodiment the antibody is a multi-specific antibody molecule comprising or consisting of:

a) a polypeptide chain of formula (I):

VH-CH1-X-V1; and b) a polypeptide chain of formula (II):

VL-CL-Y-V2;

wherein:
VH represents a heavy chain variable domain;
CH1 represents a domain of a heavy chain constant region, for example domain 1 thereof;
X represents a bond or linker;
Y represents a bond or linker;
V1 represents a dsFv, a sdAb, a scFv or a dsscFv;
VL represents a light chain variable domain;
CL represents a domain from a light chain constant region, such as Ckappa;
V2 represents dsFv, a sdAb, a scFv or a dsscFv;
wherein at least one of V1 or V2 is a dsFv or dsscFv, described in WO2015/197772 incorporated herein by reference.

"Single chain variable fragment" or "scFv" as employed herein refers to a single chain variable fragment comprising or consisting of a heavy chain variable domain (VH) and a light chain variable domain (VL) which is stabilised by a peptide linker between the VH and VL variable domains. The VH and VL variable domains may be in any suitable orientation, for example the C-terminus of VH may be linked to the N-terminus of VL or the C-terminus of VL may be linked to the N-terminus of VH.

"Disulphide-stabilised single chain variable fragment" or "dsscFv" refers to a single chain variable fragment which is stabilised by a peptide linker between the VH and VL variable domain and also includes an inter-domain disulphide bond between VH and VL.

"Disulphide-stabilised variable fragment" or "dsFv" refers to a single chain variable fragment which does not include a peptide linker between the VH and VL variable domains and is instead stabilised by an interdomain disulphide bond between VH and VL.

In one particular embodiment, the antibody is the multi-specific antibody of the format Fab-2x dsscFv described in WO2015/197772, incorporated herein by reference.

In a further particular embodiment, the multispecific antibody of the format Fab-2x dsscFv is a trivalent antibody, i.e. each Fv binds to a different epitope.

In a further particular embodiment, the multispecific antibody has a Fab-dsscFv-dsFv format as described in WO2015/197772, incorporated herein by reference.

In one embodiment, the antibody to be purified comprises a sequence selected from the group consisting of SEQ ID NO:1, SEQ ID NO:2, SEQ ID NO:3, SEQ ID NO:4, SEQ ID NO:5, and SEQ ID NO:6.

```
SEQ ID NO: 1:
(a) Heavy chain variable domain of
anti-albumin antibody (no ds)
EVQLLESGGGLVQPGGSLRLSCAVSGIDLSNYAIN

VWRQAPGKGLEWIGIIWASGTTFYATWAKGRFTIS

RDNSKNTVYLQMNSLRAEDTAVYYCARTVPGYSTA

PYFDLWGQGTLVTVSS

SEQ ID NO: 2:
(b) Heavy chain variable domain of
anti-albumin antibody (ds)
EVQLLESGGGLVQPGGSLRLSCAVSGIDLSNYAIN

VWRQAPGKCLEWIGIIWASGTTFYATWAKGRFTIS

RDNSKNTVYLQMNSLRAEDTAVYYCARTVPGYSTA

PYFDLWGQGTLVTVSS

SEQ ID NO: 3:
(c) Light chain variable domain of
anti-albumin antibody (no ds)
DIQMTQSPSSVSASVGDRVTITCQSSPSVWSNFLS

WYQQKPGKAPKLLIYEASKLTSGVPSRFSGSGSGT

DFTLTISSLQPEDFATYYCGGGYSSISDTTFGGGT

KVEIKRT

SEQ ID NO: 4:
(d) Light chain variable domain of
anti-albumin antibody (ds)
DIQMTQSPSSVSASVGDRVTITCQSSPSVWSNFLS

WYQQKPGKAPKLLIYEASKLTSGVPSRFSGSGSGT

DFTLTISSLQPEDFATYYCGGGYSSISDTTFGCGT

KVEIKRT

SEQ ID NO: 5:
645 gH5gL4 specific to albumin
EVQLLESGGGLVQPGGSLRLSCAVSGIDLSNYAIN

VWRQAPGKGLEWIGIIWASGTTFYATWAKGRFTIS

RDNSKNTVYLQMNSLRAEDTAVYYCARTVPGYSTA

PYFDLWGQGTLVTVSSGGGGSGGGGSGGGGSGGGG

SDIQMTQSPSSVSASVGDRVTITCQSSPSVWSNFL

SWYQQKPGKAPKLLIYEASKLTSGVPSRFSGSGSG

TDFTLTISSLQPEDFATYYCGGGYSSISDTTFGGG

TKVEIKRT

SEQ ID NO: 6:
645 gH5gL4ds specific to albumin
EVQLLESGGGLVQPGGSLRLSCAVSGIDLSNYAIN

WVRQAPGKCLEWIGIIWASGTTFYATWAKGRFTIS

RDNSKNTVYLQMNSLRAEDTAVYYCARTVPGYSTA

PYFDLWGQGTLVTVSSGGGGSGGGGSGGGGSGGGG

SDIQMTQSPSSVSASVGDRVTITCQSSPSVWSNFL

SWYQQKPGKAPKLLIYEASKLTSGVPSRFSGSGSG
```

-continued

TDFTLTISSLQPEDFATYYCGGGYSSISDTTFGCG

TKVEIKRT

The mixture comprising the antibody that is loaded onto the affinity chromatography resin in step a) of the method of the invention is, in many embodiments, directly or indirectly derived from a cell culture (e.g. a mammalian or bacterial culture) wherein the antibody is produced recombinantly.

A recombinant antibody or antibody derivative, such as an antibody fragment, manufactured for large-scale commercial purposes can be produced by culturing eukaryotic host cells transfected with one or more expression vectors encoding the recombinant antibody. The eukaryotic host cells are preferably mammalian cells, more preferably Chinese Hamster Ovary (CHO) cells.

Mammalian cells may be cultured in any medium that will support their growth and expression of the antibody, preferably the medium is a chemically defined medium that is free of animal-derived products such as animal serum and peptone. There are different cell culture mediums available to the person skilled in the art comprising different combinations of vitamins, amino acids, hormones, growth factors, ions, buffers, nucleosides, glucose or an equivalent energy source, present at appropriate concentrations to enable cell growth and protein production. Additional cell culture media components may be included in the cell culture medium at appropriate concentrations at different times during a cell culture cycle that would be known to those skilled in the art.

Mammalian cell culture can take place in any suitable container such as a shake flask or a bioreactor, which may or may not be operated in a fed-batch mode depending on the scale of production required. These bioreactors may e.g. be stirred-tank or air-lift reactors. Various large scale bioreactors are available with a capacity of more than 1,000 L to 50,000 L, preferably between 5,000 L and 20,000 L, or to 10,000 L. Alternatively, bioreactors of a smaller scale such as between 2 L and 100 L may also be used to manufacture an antibody to be purified according to the method of the invention.

An antibody or antigen-binding fragment thereof that can be manufactured in accordance with the methods of the present invention is typically found in the supernatant of a mammalian host cell culture, typically a CHO cell culture. For CHO culture processes wherein the protein of interest such as an antibody or antigen-binding fragment thereof is secreted in the supernatant, said supernatant is collected by methods known in the art, typically by centrifugation. For avoidance of doubt, supernatant denotes the liquid lying above the sedimented cells resulting from the centrifugation of the cell culture.

In one embodiment of the invention, the method comprises culturing CHO cells that express the antibody of interest, recovering the supernatant, and purifying said antibody from the mixture wherein said purification comprises at least one affinity chromatography step performed according to the method of the invention.

Alternatively, host cells are preferably prokaryotic cells, preferably Gram-negative bacteria. More preferably, the host cells are E. coli cells. Prokaryotic host cells for protein expression are well known in the art (Terpe, K. (2006). Overview of bacterial expression systems for heterologous protein production: from molecular and biochemical fundamentals to commercial systems. Appl Microbiol Biotechnol 72, 211-222.). The host cells are recombinant cells which have been genetically engineered to produce the protein of interest such as an antibody fragment. The recombinant E. coli host cells may be derived from any suitable E. coli strain including from MC4100, TG1, TG2, DHB4, DH5α, DH1, BL21, K12, XL1Blue and JM109. One example is E. coli strain W3110 (ATCC 27,325) a commonly used host strain for recombinant protein fermentations. Antibody fragments can also be produced by culturing modified E. coli strains, for example metabolic mutants or protease deficient E. coli strains.

An antibody fragment that can be purified in accordance with the methods of the present invention is typically found in either the periplasm of the E. coli host cell or in the host cell culture supernatant, depending on the nature of the protein, the scale of production and the E. coli strain used. The methods for targeting proteins to these compartments are well known in the art (Makrides, S.C. (1996). Strategies for achieving high-level expression of genes in Escherichia coli. Microbiol Rev 60, 512-538.). Examples of suitable signal sequences to direct proteins to the periplasm of E. coli include the E. coli PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelB leader, the protein A leader, the co-expression of bacteriocin release protein, the mitomycin-induced bacteriocin release protein along with the addition of glycine to the culture medium and the co-expression of the kil gene for membrane permeabilization. Most preferably, in the methods of the invention, the antibody is expressed in the periplasm of the host E. coli.

Expression of the antibody in the E. coli host cells may also be under the control of an inducible system, whereby the expression of the recombinant antibody in E. coli is under the control of an inducible promoter. Many inducible promoters suitable for use in E. coli are well known in the art and depending on the promoter expression of the recombinant protein can be induced by varying factors such as temperature or the concentration of a particular substance in the growth medium. Examples of inducible promoters include the E. coli lac, tac, and trc promoters which are inducible with lactose or the non-hydrolyzable lactose analog, isopropyl-b-D-1-thiogalactopyranoside (IPTG) and the phoA, trp and araBAD promoters which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer.

E. coli host cell cultures (fermentations) may be cultured in any medium that will support the growth of E. coli and expression of the recombinant protein. The medium may be any chemically defined medium such as e.g. described in Durany O,C.G.d.M.C.L.-S.J. (2004). Studies on the expression of recombinant fuculose-1-phosphate aldolase in Escherichia coli. Process Biochem 39, 1677-1684.

Culturing of the E. coli host cells can take place in any suitable container such as a shake flask or a fermenter depending on the scale of production required. Various large scale fermenters are available with a capacity of more than 1,000 liters up to about 100,000 liters. Preferably, fermenters of 1,000 to 50,000 liters are used, more preferably 1,000 to 25,000, 20,000, 15,000, 12,000 or 10,000 liters. Smaller scale fermenters may also be used with a capacity of between 0.5 and 1,000 liters.

Fermentation of E. coli may be performed in any suitable system, for example continuous, batch or fed-batch mode depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete. Fed-batch mode may also be used pre-induction to control the metabolism of the E. coli host cells and to allow higher cell densities to be reached.

If desired, the host cells may be subject to collection from the fermentation medium, e.g. host cells may be collected from the sample by centrifugation, filtration or by concentration.

In one embodiment the process according to the present invention comprises a step of centrifugation and cell recovery prior to extracting the antibody.

For E. coli fermentation processes wherein the protein of interest such as an antibody fragment is found in the periplasmic space of the host cell it is required to release the protein from the host cell. The release may be achieved by any suitable method such as cell lysis by mechanical or pressure treatment, freeze-thaw treatment, osmotic shock, extraction agents or heat treatment. Such extraction methods for protein release are well known in the art.

In a further embodiment, the method according to the invention further comprises recovering the host cells from the cell culture medium, harvesting the protein using a protein extraction step performed in the presence of a reducing agent, recovering the antibody-containing mixture resulting from the protein extraction step and purifying said antibody from the mixture wherein said purification comprises at least one affinity chromatography step performed according to the method of the invention.

EXAMPLES

Example 1

Static Binding MODDE Study

Method

PrA MabSelect SuRe resin, GE, were used in a static binding mode (CV=1 mL). A MODDE DoE study was designed testing four imidazole elution buffers (N1-N4), with a fifth buffer used in triplicate for the center point (N5-N7) (Table 1). The resin was equilibrated with 100 mM Sodium Phosphate pH 7.0. A monoclonal IgG1 antibody was loaded onto the resin at 40 g/L resin. The resin was then washed with 100 mM Sodium Phosphate pH 7.0. Elution was performed one of the five buffers, with four sequential elution cycles being performed to maximize recovery. Total amounts eluted were then calculated for each elution cycle.

TABLE 1

Static Binding MODDE Study Data

| Experiment Name | pH | Imidazole (mM) | Cycle 1 Amount (mg) | Cycle 2 Amount (mg) | Cycle 3 Amount (mg) | Cycle 4 Amount (mg) | Total Yield (%) |
|---|---|---|---|---|---|---|---|
| N1 | 3.6 | 0.0 | 2.91 | 10.15 | 10.50 | 5.66 | 73 |
| N2 | 4.0 | 0.0 | 2.75 | 2.92 | 2.71 | 2.05 | 26. |
| N3 | 3.6 | 250 | 4.66 | 13.23 | 8.10 | 3.54 | 74 |
| N4 | 4.0 | 250 | 1.99 | 4.02 | 4.22 | 3.49 | 34 |
| N5 | 3.8 | 0.0 | 2.30 | 6.04 | 5.70 | 4.70 | 47 |
| N6 | 3.8 | 0.0 | 1.82 | 5.09 | 5.92 | 4.50 | 43 |
| N7 | 3.8 | 0.0 | 2.37 | 6.29 | 6.21 | 4.65 | 49 |

Results & Conclusions

FIG. 1 is a coefficient plot generated from the data in Table 1 in the MODDE analysis software. Each bar represents one of the parameters investigated and what happens to the measured factor when the value of the parameter is increased. A positive bar indicates that a higher value of the parameter increases the value of the measured factor, whereas a negative bar indicates that a higher value of the parameter reduces the measured factor.

FIG. 1 shows that imidazole has a statically significant effect on amount recovered at cycles 1 & 2. But not at cycles 3 & 4, as most of the product had eluted, producing comparable amounts during these steps as without imidazole being present. A high pH negatively effects the amount eluted and recovery, but the addition of imidazole can counteract this effect. As more of the IgG1 is recovered in the earlier cycles, imidazole allows for a reduction in the number of cycles and thus elution volume, due to its faster elution kinetics. For example, at pH 4.0 with imidazole only 3 cycles are required to reach the same amount compared to without imidazole for 4 cycles.

Example 2

IgG Chromatogram Elution Profile

Method

Two MabSelect SuRe HiScreen columns, GE, (9.4 mL CV) were used in a dynamic binding mode. The resin was equilibrated with 100 mM Sodium Phosphate pH 7.0. A monoclonal antibody, IgG1 or a IgG4, was loaded onto the resin at 50 g/L resin. The resin was then washed with 100 mM Sodium Phosphate pH 7.0, followed by a salt wash with 100 mM Sodium phosphate and 500 mM Sodium Chloride pH 6.9. Elution was performed with either 100 mM Sodium Citrate at pH 3.6 or pH 4.0 (adjusted with NaOH) or with 100 mM Sodium Citrate with 300 mM Imidazole at pH 3.6 or pH 4.0 (adjusted with HCl).

Results & Conclusions

Figure 2:
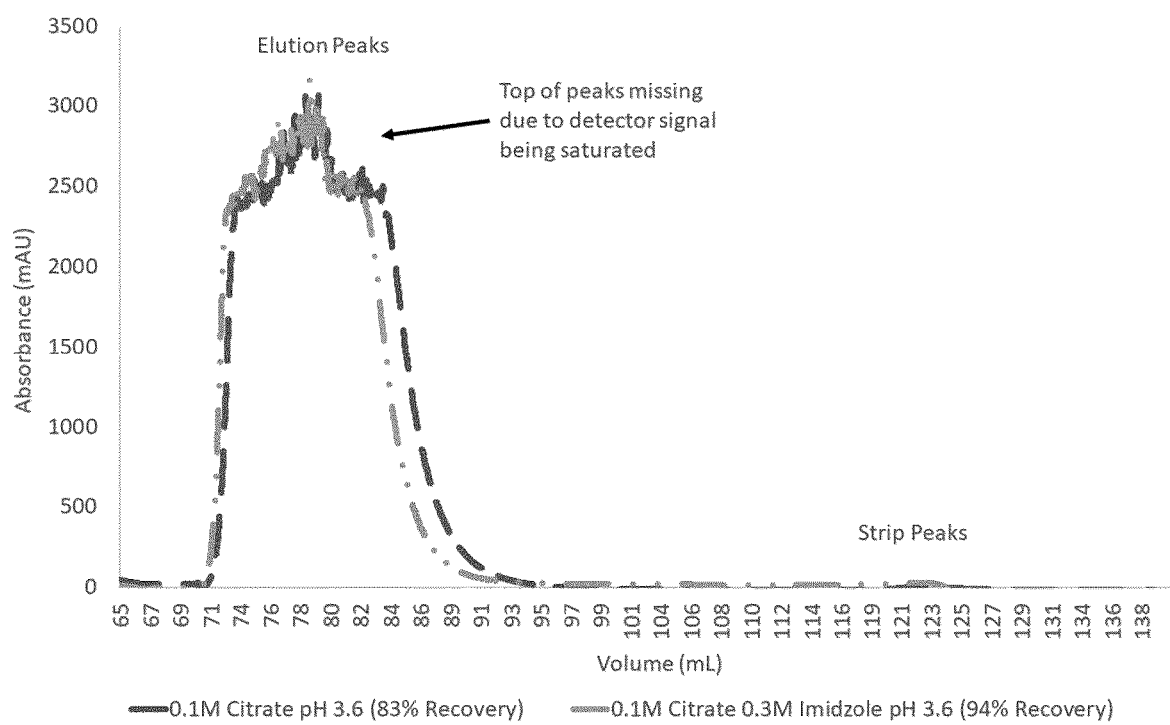
FIG. 2: IgG1 Chromatogram Elution Profile Overlay at pH 3.6+/− Imidazole
Figure 3:
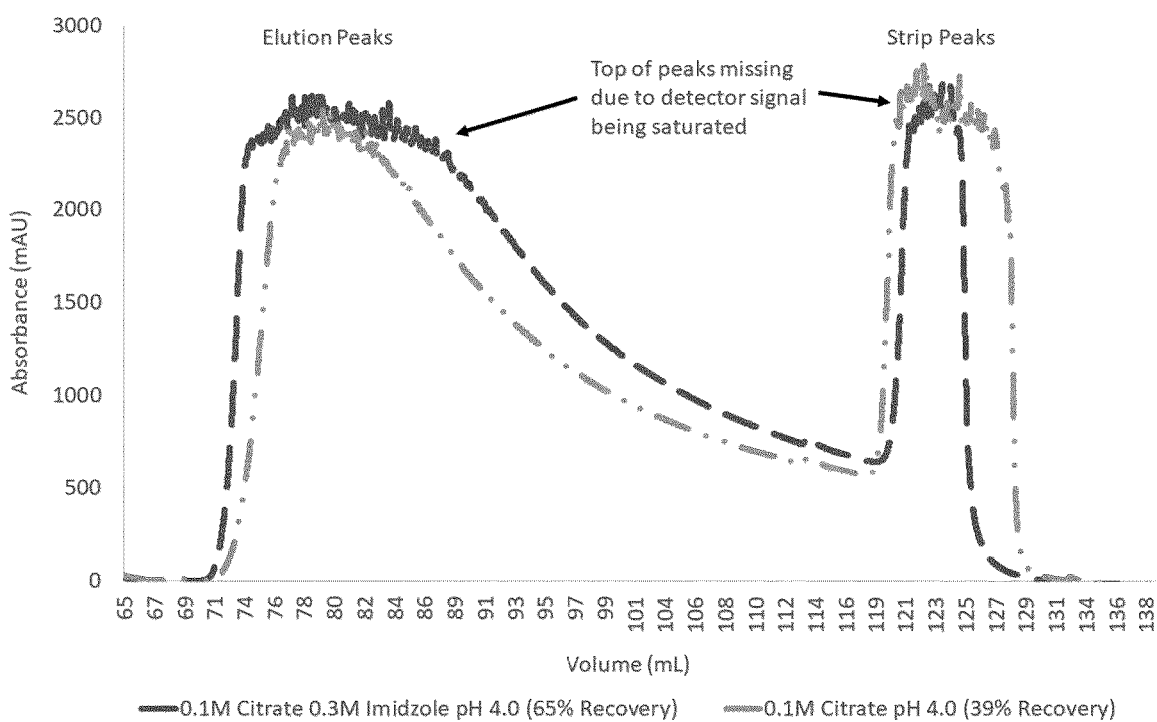
FIG. 3: IgG1 Chromatogram Elution Profile Overlay at pH 4.0+/− Imidazole
Figure 4:
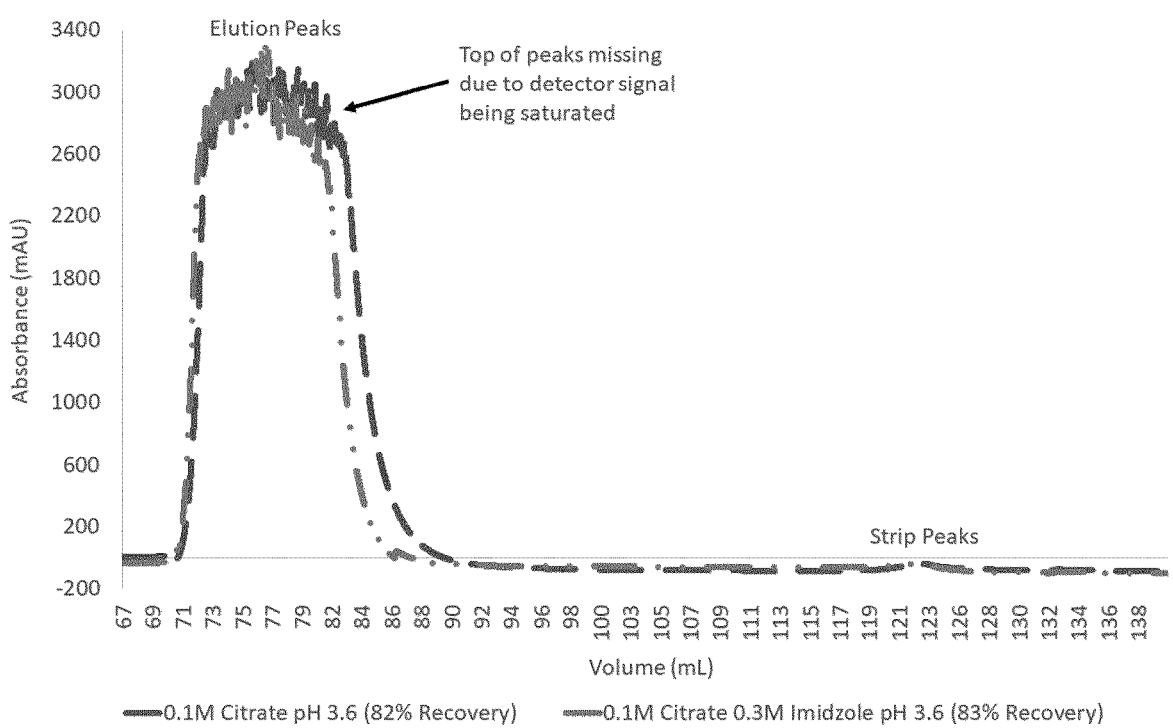
FIG. 4: IgG4 Chromatogram Elution Profile Overlay at pH 3.6+/− Imidazole

FIGS. 2 & 3 show the results obtained for an IgG1 monoclonal antibody: the citrate elution recovered 83% of product at pH 3.6 and 39% at pH 4.0. However, by adding imidazole these yields have increased to 94% and 65% respectively. In addition, at pH 3.6 the elution volume is decreased with the addition of imidazole. The elution volume at pH 4.0 with imidazole is larger than the buffer without, this is because more product has eluted and for the run without imidazole to reach the same recovery a near infinite elution volume would be required, as it has slower elution kinetics. FIG. 4 shows that equivalent results were obtained with an IgG4.

Example 3

VH3 Chromatogram Elution Profile

Method

Two MabSelect HiScreen columns, GE, (9.4 mL CV) were used in a dynamic binding mode. The resin was equilibrated with 100 mM Sodium Phosphate pH 7.0. A multispecific trivalent antibody molecule of the format Fab-2x dsscFv, as described in WO2015/197772 (TrYbe®), was loaded onto the resin at 30 g/L resin. The resin was then washed with 100 mM Sodium Phosphate pH 7.0. Elution was performed with either 100 mM Sodium Citrate at pH 4.0 (adjusted with NaOH) or with 100 mM Sodium Citrate with 300 mM Imidazole at pH 4.0 (adjusted with HCl).

Results & Conclusions

Figure 5:
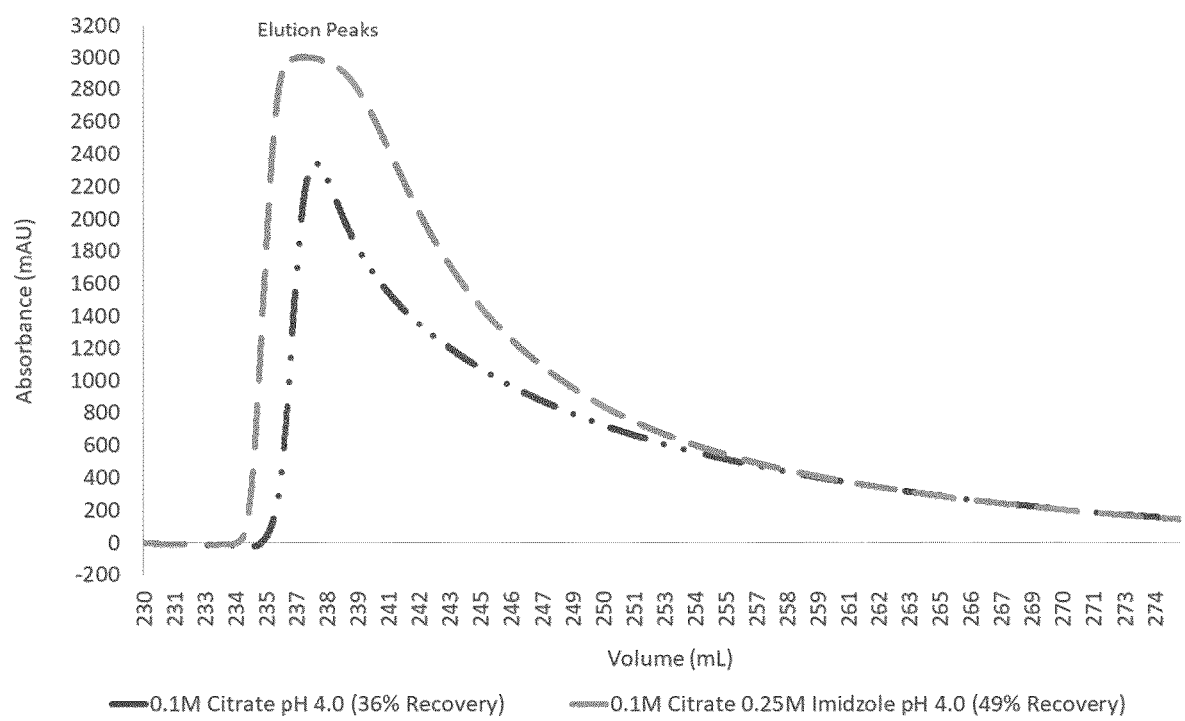
FIG. 5: TrYbe (VH3) Chromatogram Elution Profile Overlay at pH 4.0+/− Imidazole

FIG. 5 shows that the citrate elution recovered 36% of product at pH 4.0. However, by adding imidazole the yield increased to 49% in the same volume of elution buffer. Therefore, the addition of imidazole has increased the elution kinetics allowing more product to elute faster and thus required less buffer to achieve the same recovery. In addition, this experiment has shown that imidazole can prevent the rebinding of product to the resin ligand through Fc and VH3 binding sites.

Example 4

IgG MODDE Study

Method

Two MabSelect SuRe HiScreen columns, GE, (9.4 mL CV) were used in a dynamic binding mode. The resin was equilibrated with 100 mM Sodium Phosphate pH 7.0. A monoclonal antibody, IgG1, was loaded onto the resin at 50 g/L resin. The resin was then washed with 100 mM Sodium Phosphate pH 7.0, followed by a salt wash with 100 mM Sodium phosphate 500 mM Sodium Chloride pH 6.9. A range of different 0.1 M citrate elution buffers were tested in a DoE with varying imidazole concentrations and pH values (Table 2). An additional imidazole wash buffer was tested, replacing the final pre-elution wash, to investigate whether pre-loading the column with imidazole had a greater effect on the elution kinetics.

TABLE 2

Dynamic Binding MODDE Study Data

| Experiment Name | Imidazole Elution (M) | pH | Imidazole Wash (M) | Yield (%) | Elution Volume (CV) | Total Eluate Concentration (mg/mL) |
|---|---|---|---|---|---|---|
| N1 | 0.00 | 3.50 | 0.00 | 84 | 1.9 | 16.0 |
| N2 | 0.50 | 3.50 | 0.00 | 98 | 2.1 | 16.5 |
| N3 | 0.00 | 4.00 | 0.00 | 58 | 19.0 | 1.1 |
| N4 | 0.50 | 4.00 | 0.00 | 69 | 10.4 | 2.3 |
| N5 | 0.00 | 3.50 | 0.25 | 97 | 2.1 | 16.5 |
| N6 | 0.50 | 3.50 | 0.25 | 92 | 1.8 | 18.3 |
| N7 | 0.00 | 4.00 | 0.25 | 59 | 15.9 | 1.3 |
| N8 | 0.50 | 4.00 | 0.25 | 90 | 8.4 | 3.7 |
| N9 | 0.25 | 3.75 | 0.00 | 96 | 3.7 | 9.1 |
| N10 | 0.25 | 3.75 | 0.00 | 95 | 3.6 | 9.2 |
| N11 | 0.25 | 3.75 | 0.00 | 96 | 3.8 | 8.7 |
| N12 | 0.00 | 3.75 | 0.00 | 99 | 6.5 | 5.4 |
| N13 | 0.50 | 3.75 | 0.25 | 94 | 2.5 | 13.0 |
| N14 | 0.25 | 3.50 | 0.00 | 100 | 1.8 | 19.2 |
| N15 | 0.25 | 4.00 | 0.25 | 98 | 9.9 | 3.5 |
| N16 | 0.25 | 4.00 | 0.00 | 101 | 12.0 | 2.9 |
| N17 | 0.00 | 3.75 | 0.25 | 99 | 5.4 | 6.4 |
| N18 | 0.50 | 3.75 | 0.00 | 103 | 2.7 | 13.4 |
| N19 | 0.25 | 3.50 | 0.25 | 102 | 1.7 | 20.6 |
| N20 | 0.25 | 3.75 | 0.00 | 103 | 3.2 | 11.2 |
| N21 | 0.50 | 3.50 | 0.00 | 102 | 2.2 | 16.1 |

Results & Conclusions

Figure 6:
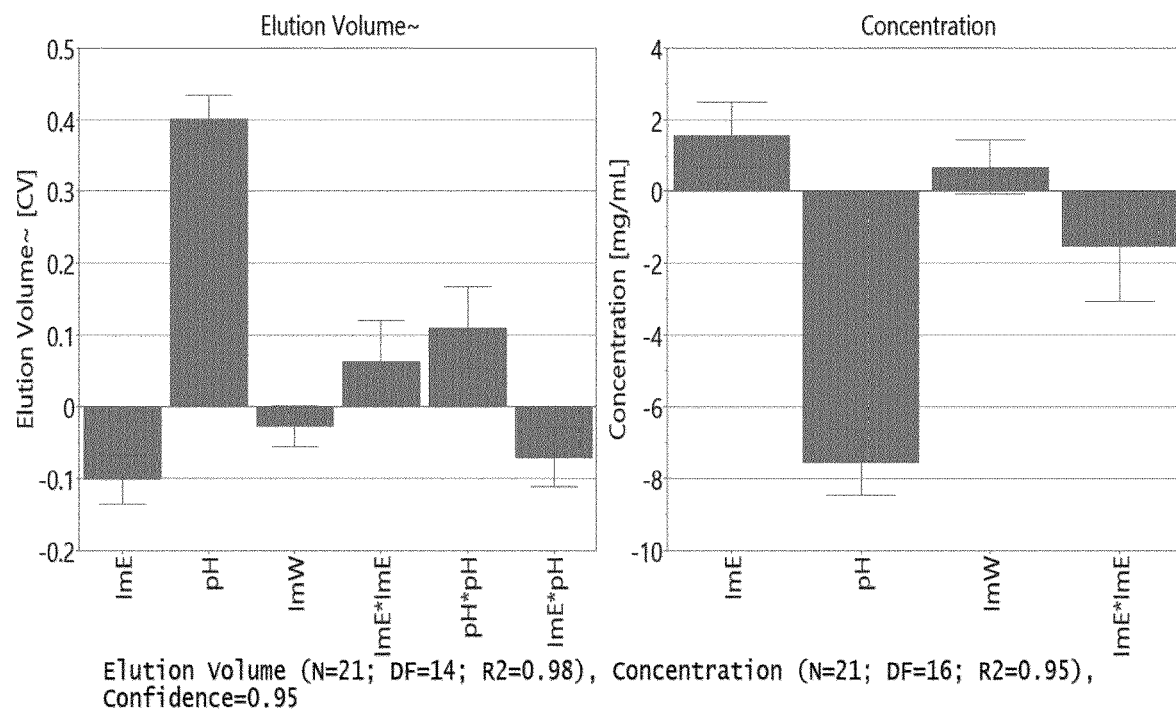
FIG. 6: Dynamic Binding Study Results

FIG. 6 is a coefficient plot generated in the MODDE analysis software in the same way as FIG. 1, but using the data in Table 2. "ImE" is Imidazole concentration in elution buffer and "ImW" is Imidazole concentration in the wash buffer. "*" indicates an interaction between the term (s).

FIG. 6 show the result from the MODDE study, which further supports the previous experiments as it determined that imidazole has a statically significant effect on reducing elution volume, thus increasing product concentration in the eluate. The study also determined a squared term for the Imidazole concentration (ImE*ImE), which shows that there is an optimum concentration to use and deviating away from this range will result in an increase in elution volume. In addition, washing the column with an imidazole buffer prior to eluting further reduced elution volume. Pre-loading imidazole on the column, before the elution step, prevents the elution front that is moving down the column from being in an imidazole free environment. Thus, pre-loading with imidazole allows all aspects of the elution step to be prevented from rebinding to the resin, which therefore increases the elution kinetics.

Example 5

Imidazole Analog Elution Profile

Method

Two MabSelect HiScreen columns, GE, (9.4 mL CV) were used in a dynamic binding mode. The resin was equilibrated with 100 mM Sodium Phosphate pH 7.0. A monoclonal antibody, IgG1, was loaded onto the resin at 35 g/L resin. The resin was then washed with 100 mM Sodium Phosphate pH 7.0. Elution was performed with either 100 mM Sodium Citrate at pH 3.6 or with 100 mM Sodium Citrate with 250 mM 1,3 dimethyl-1H-pyrazole at pH 3.6. This analog was deemed to be effective at reducing elution volume in a preliminary analog study.

Results & Conclusions

Figure 7:
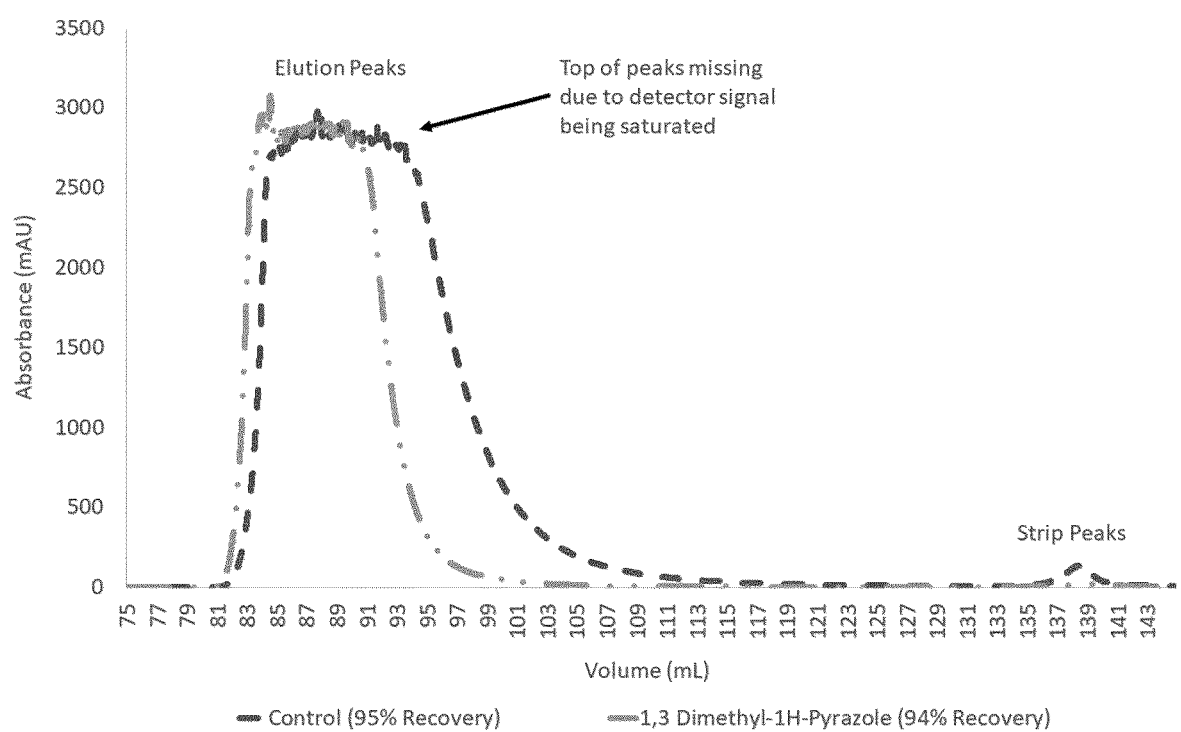
FIG. 7: IgG1 Chromatogram Elution Profile Overlay at pH 3.6+/−1,3 dimethyl-1H-pyrazole

FIG. 7 shows that the control citrate elution recovered 95% of product at pH 3.6 in 2.85 column volumes. However, by adding 1,3 dimethyl-1H-pyrazole the elution volume was reduced to 1.76 column columns with a comparable recovery of 94%. Therefore, the addition of 1,3 dimethyl-1H-pyrazole has increased the elution kinetics allowing the product to elute faster and thus required less buffer to achieve a similar recovery.

The invention claimed is:

1. A method for purifying an antibody comprising:
   a) loading a mixture comprising the antibody to be purified onto an affinity chromatography resin, wherein the affinity chromatography resin is selected from: a protein A chromatography resin, a protein G chromatography resin or a protein L chromatography resin;

b) washing the chromatographic resin with a wash buffer; and c) eluting the antibody with an elution buffer that comprises 0.01M to 1.0M imidazole or an imidazole-analogue and a pH of 3 to 5, wherein the imidazole analogue is selected from 4 (5)-methylimidazole, pyrazole, 1,5-dimethyl-1H-pyrazole, 1,3-dimethyl-1H-pyrazole or 1H-Imidazole-1-ylmethanol.

2. The method according to claim 1, wherein the elution buffer comprises 0.01M to 0.5M imidazole or an imidazole-analogue.

3. The method according to claim 1, wherein the wash buffer comprises imidazole or an imidazole-analogue.

4. The method according to claim 3, wherein the wash buffer comprises 0.01M to 0.5M imidazole or an imidazole-analogue.

5. The method according to claim 1, wherein the method comprises a further step of equilibrating the chromatographic resin with an equilibration buffer comprising imidazole or an imidazole-analogue prior to loading of the mixture comprising the antibody onto the chromatographic resin.

6. The method according to claim 1, wherein one, two of all of, of steps a), b) and c) are performed under dynamic conditions.

7. The method according to claim 1, wherein the antibody is selected from: IgG, Fab', F(ab')2, scFv, Fab-Fv, Fab-scFv, Fab-(scFv)2, Fab-(Fv)2, diabodies, triabodies, and tetrabodies.

* * * * *

```
                         SEQUENCE LISTING

<160> NUMBER OF SEQ ID NOS: 9

<210> SEQ ID NO 1
    <211> LENGTH: 121
    <212> TYPE: PRT
    <213> ORGANISM: Artificial Sequence
    <220> FEATURE:
    <223> OTHER INFORMATION: ) Heavy chain variable domain of anti-albumin
          antibody (no ds)

<400> SEQUENCE: 1

Glu Val Gln Leu Leu Glu Ser Gly Gly Gly Leu Val Gln Pro Gly Gly
    1               5                   10                  15

Ser Leu Arg Leu Ser Cys Ala Val Ser Gly Ile Asp Leu Ser Asn Tyr
                20                  25                  30

Ala Ile Asn Trp Val Arg Gln Ala Pro Gly Lys Gly Leu Glu Trp Ile
                35                  40                  45

Gly Ile Ile Trp Ala Ser Gly Thr Thr Phe Tyr Ala Thr Trp Ala Lys
        50                  55                  60

Gly Arg Phe Thr Ile Ser Arg Asp Asn Ser Lys Asn Thr Val Tyr Leu
    65                  70                  75                  80

Gln Met Asn Ser Leu Arg Ala Glu Asp Thr Ala Val Tyr Tyr Cys Ala
                    85                  90                  95

Arg Thr Val Pro Gly Tyr Ser Thr Ala Pro Tyr Phe Asp Leu Trp Gly
                100                 105                 110

Gln Gly Thr Leu Val Thr Val Ser Ser
                115                 120

<210> SEQ ID NO 2
    <211> LENGTH: 121
    <212> TYPE: PRT
    <213> ORGANISM: Artificial Sequence
    <220> FEATURE:
    <223> OTHER INFORMATION: Heavy chain variable domain of anti-albumin
          antibody (ds)

<400> SEQUENCE: 2

Glu Val Gln Leu Leu Glu Ser Gly Gly Gly Leu Val Gln Pro Gly Gly
    1               5                   10                  15

Ser Leu Arg Leu Ser Cys Ala Val Ser Gly Ile Asp Leu Ser Asn Tyr
                20                  25                  30

Ala Ile Asn Trp Val Arg Gln Ala Pro Gly Lys Cys Leu Glu Trp Ile
                35                  40                  45

Gly Ile Ile Trp Ala Ser Gly Thr Thr Phe Tyr Ala Thr Trp Ala Lys
        50                  55                  60

Gly Arg Phe Thr Ile Ser Arg Asp Asn Ser Lys Asn Thr Val Tyr Leu
```

```
                65                  70                  75                  80
        Gln Met Asn Ser Leu Arg Ala Glu Asp Thr Ala Val Tyr Tyr Cys Ala
                        85                  90                  95

Arg Thr Val Pro Gly Tyr Ser Thr Ala Pro Tyr Phe Asp Leu Trp Gly
                        100                 105                 110

Gln Gly Thr Leu Val Thr Val Ser Ser
                        115                 120

<210> SEQ ID NO 3
<211> LENGTH: 112
<212> TYPE: PRT
<213> ORGANISM: Artificial Sequence
<220> FEATURE:
<223> OTHER INFORMATION: Light chain variable domain of anti-albumin
      antibody (no ds)

<400> SEQUENCE: 3

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
                20                  25                  30

Phe Leu Ser Trp Tyr Gln Gln Lys Pro Gly Lys Ala Pro Lys Leu Leu
            35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Gly Gly Thr Lys Val Glu Ile Lys Arg Thr
                100                 105                 110

<210> SEQ ID NO 4
<211> LENGTH: 112
<212> TYPE: PRT
<213> ORGANISM: Artificial Sequence
<220> FEATURE:
<223> OTHER INFORMATION: Light chain variable domain of anti-albumin
      antibody (ds)

<400> SEQUENCE: 4

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
                20                  25                  30

Phe Leu Ser Trp Tyr Gln Gln Lys Pro Gly Lys Ala Pro Lys Leu Leu
            35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Cys Gly Thr Lys Val Glu Ile Lys Arg Thr
                100                 105                 110

<210> SEQ ID NO 5
<211> LENGTH: 253
<212> TYPE: PRT
```

<213> ORGANISM: Artificial Sequence
<220> FEATURE:
<223> OTHER INFORMATION: 645 gH5gL4 specific to albumin

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gly Gly Gly Ser Asp Ile Gln
    130                 135                 140

Met Thr Gln Ser Pro Ser Ser Val Ser Ala Ser Val Gly Asp Arg Val
145                 150                 155                 160

Thr Ile Thr Cys Gln Ser Ser Pro Ser Val Trp Ser Asn Phe Leu Ser
                165                 170                 175

Trp Tyr Gln Gln Lys Pro Gly Lys Ala Pro Lys Leu Leu Ile Tyr Glu
            180                 185                 190

Ala Ser Lys Leu Thr Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gly Gly Gly Tyr Ser Ser Ile Ser Asp Thr
225                 230                 235                 240

Thr Phe Gly Gly Gly Thr Lys Val Glu Ile Lys Arg Thr
                245                 250
```

<210> SEQ ID NO 6
<211> LENGTH: 253
<212> TYPE: PRT
<213> ORGANISM: Artificial Sequence
<220> FEATURE:
<223> OTHER INFORMATION: 645 gH5gL4ds specific to albumin

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80
```

```
Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Ser Gly Gly Gly Ser Asp Ile Gln
    130                 135                 140

Met Thr Gln Ser Pro Ser Val Ser Ala Ser Val Gly Asp Arg Val
145                 150                 155                 160

Thr Ile Thr Cys Gln Ser Pro Ser Val Trp Ser Asn Phe Leu Ser
                165                 170                 175

Trp Tyr Gln Gln Lys Pro Gly Lys Ala Pro Lys Leu Leu Ile Tyr Glu
            180                 185                 190

Ala Ser Lys Leu Thr Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
        210                 215                 220

Phe Ala Thr Tyr Tyr Cys Gly Gly Gly Tyr Ser Ser Ile Ser Asp Thr
225                 230                 235                 240

Thr Phe Gly Cys Gly Thr Lys Val Glu Ile Lys Arg Thr
                245                 250

<210> SEQ ID NO 7
<211> LENGTH: 6
<212> TYPE: PRT
<213> ORGANISM: Artificial Sequence
<220> FEATURE:
<223> OTHER INFORMATION: HQ motif

<400> SEQUENCE: 7

His Gln His Gln His Gln
1               5

<210> SEQ ID NO 8
<211> LENGTH: 6
<212> TYPE: PRT
<213> ORGANISM: Artificial Sequence
<220> FEATURE:
<223> OTHER INFORMATION: HN motif

<400> SEQUENCE: 8

His Asn His Asn His Asn
1               5

<210> SEQ ID NO 9
<211> LENGTH: 19
<212> TYPE: PRT
<213> ORGANISM: Artificial Sequence
<220> FEATURE:
<223> OTHER INFORMATION: HAT motif

<400> SEQUENCE: 9

Lys Asp His Leu Ile His Asn Val His Lys Glu Glu His Ala His Ala
1               5                   10                  15

His Asn Lys
```